(12) United States Patent
Clark et al.

(10) Patent No.: US 6,826,972 B2
(45) Date of Patent: Dec. 7, 2004

(54) LYSIMETER METHODS AND APPARATUS

(75) Inventors: Don T. Clark, Idaho Falls, ID (US); Eugene E. Erickson, Pocatello, ID (US); William L. Casper, Rigby, ID (US); David M. Everett, Shelley, ID (US); Joel M. Hubbell, Idaho Falls, ID (US); James B. Sisson, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 10/285,798

(22) Filed: Oct. 31, 2002

(65) Prior Publication Data

US 2004/0083827 A1 May 6, 2004

(51) Int. Cl.[7] .............................. G01N 1/26; E21B 49/00
(52) U.S. Cl. ................................. 73/863.81; 73/152.23; 175/59
(58) Field of Search .................. 175/59, 60; 73/152.23, 73/152.24, 152.25, 152.26, 863.81, 864.34, 864.74

(56) References Cited

U.S. PATENT DOCUMENTS

| | | | | |
|---|---|---|---|---|
| 4,669,554 A | * | 6/1987 | Cordry ........................ 175/59 |
| 4,807,707 A | * | 2/1989 | Handley et al. ............... 175/20 |
| 5,046,568 A | * | 9/1991 | Cordry ........................ 175/21 |
| 5,337,838 A | * | 8/1994 | Sorensen ...................... 175/59 |
| 5,465,628 A | * | 11/1995 | Timmons ................. 73/864.34 |
| 5,503,031 A | * | 4/1996 | Scott et al. .............. 73/864.74 |
| 5,889,217 A | * | 3/1999 | Rossabi et al. .......... 73/864.74 |

OTHER PUBLICATIONS

Wisconsin Dept. of Natural Resources, Groundwater Sampling Desk Reference, PUBL-DG-037 96, Sep. 1996.*
Roger Davis and Tom Oothoudt, "Drilling method may be gold at end of rainbow for difficult terrains—option exists for dilling and collecting samples on one rig", Soil & Groundwater Cleanup, May 1997, pp. 34–36.*

* cited by examiner

Primary Examiner—Charles D. Garber
(74) Attorney, Agent, or Firm—Wells, St. John P.S.

(57) ABSTRACT

A suction lysimeter for sampling subsurface liquids includes a lysimeter casing having a drive portion, a reservoir portion, and a tip portion, the tip portion including a membrane through which subsurface liquids may be sampled; a fluid conduit coupled in fluid flowing relation relative to the membrane, and which in operation facilitates the delivery of the sampled subsurface liquids from the membrane to the reservoir portion; and a plurality of tubes coupled in fluid flowing relation relative to the reservoir portion, the tubes in operation facilitating delivery of the sampled subsurface liquids from the reservoir portion for testing. A method of sampling subsurface liquids comprises using this lysimeter.

11 Claims, 3 Drawing Sheets

LYSIMETER METHODS AND APPARATUS

GOVERNMENT RIGHTS

This invention was made with Government support under Contract DE-AC07-99ID13727 awarded by the U.S. Department of Energy. The Government has certain rights in the invention.

TECHNICAL FIELD

The invention relates to methods and apparatus for subsurface testing. More specifically the invention relates to methods and apparatus for sampling subsurface liquids.

BACKGROUND OF THE INVENTION

Water and associated contaminants seep into the ground and travel through a subsurface region known as the vadose zone (a region of unsaturated soil). How the water and associated contaminants move in the vadose zone, to a large degree, determines how much contamination (such as gasoline additives, agricultural chemicals, or buried waste leakage) may end up in a water supply (such as an aquifer). Therefore, gaining an understanding of how the water and associated contaminants move in the vadose zone is valuable for appropriate waste containment. Information regarding the movement of water and associated contaminants in the vadose zone is generally acquired through the use of subsurface probes or similar testing devices. Several apparatus and methods have been used to facilitate such testing and information gathering. Some of these apparatus and methods involve obtaining samples of subsurface liquids, while others test soil moisture or other parameters.

In regard to sampling subsurface liquids, various methods and apparatus have been employed, including extraction of a soil core, introduction of vacuum-based or absorptive devices or materials, use of suction lysimeters, solution samplers, and other methods. Although there are several types of lysimeters, the term "lysimeter," will be used in this document to refer to a suction lysimeter.

The suction lysimeter is a hydrological instrument used to sample liquids or to monitor soil or like substrates. The lysimeter accomplishes this function by application of vacuum or pressure gradient principles such that the liquid of interest is drawn toward the lysimeter permitting collection of a liquid sample. Although the lysimeter is primarily a sampling device, it may also be used to provide an indication of the water pressure (positive or negative). This is done by applying a vacuum, allowing the sampler to pressure equilibrate with the surrounding material being sampled, and recording this pressure.

Although prior lysimeters have been useful in gathering much information, such lysimeters have several shortcomings which have limited their usefulness. For example, prior lysimeters cannot be installed without prior excavation or drilling, and in contaminated areas such excavation or drilling is highly undesirable as it would tend to spread contamination. Additionally, such lysimeters have provided only small samples of subsurface liquids.

Another problem is that lysimeters are very fragile. They are made of ceramic, tin, copper, plastics, or similar such materials and cannot be installed directly through difficult materials such as hardened soils, concrete, steel, other metals, or waste products.

Monitoring and testing to determine the movement of subsurface water and associated contaminants is particularly valuable when dealing with waste disposal sites that contain radiological contaminants or other hazards. However, as described above, placing probes into the subsurface for data collection in such sites has not been feasible, because the placing of such probes would require drilling or coring which would bring contaminated "cuttings" to the surface and would create a pathway through which contaminated emissions may escape. As a result, test probes have typically been placed in areas around such waste sites. Unfortunately, such probe placement only provides information when the contaminants have already migrated outside of the waste disposal site area. Moreover, at the point when the contaminants have already migrated outside of the waste disposal site area, it is likely that a major contaminant plume already exists in the subsurface soil and aquifer making remediation and containment efforts much more difficult and costly.

In view of the foregoing, it would be highly desirable to provide methods and apparatus which facilitate subsurface testing and sampling in both contaminated and non-contaminated areas, while substantially avoiding these and other shortcomings of the prior devices.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The invention relates to methods and apparatus for subsurface testing. More specifically, the invention relates to methods and apparatus for sampling subsurface liquids from the substrate. One embodiment of the invention allows such sampling to be carried out in either contaminated or non-contaminated sites without the need for drilling, coring, or prior excavation. In one embodiment, a method includes placing the instrumented probe into the substrate using direct push, sonic drilling, or a combination of direct push and sonic drilling.

Figure 1:
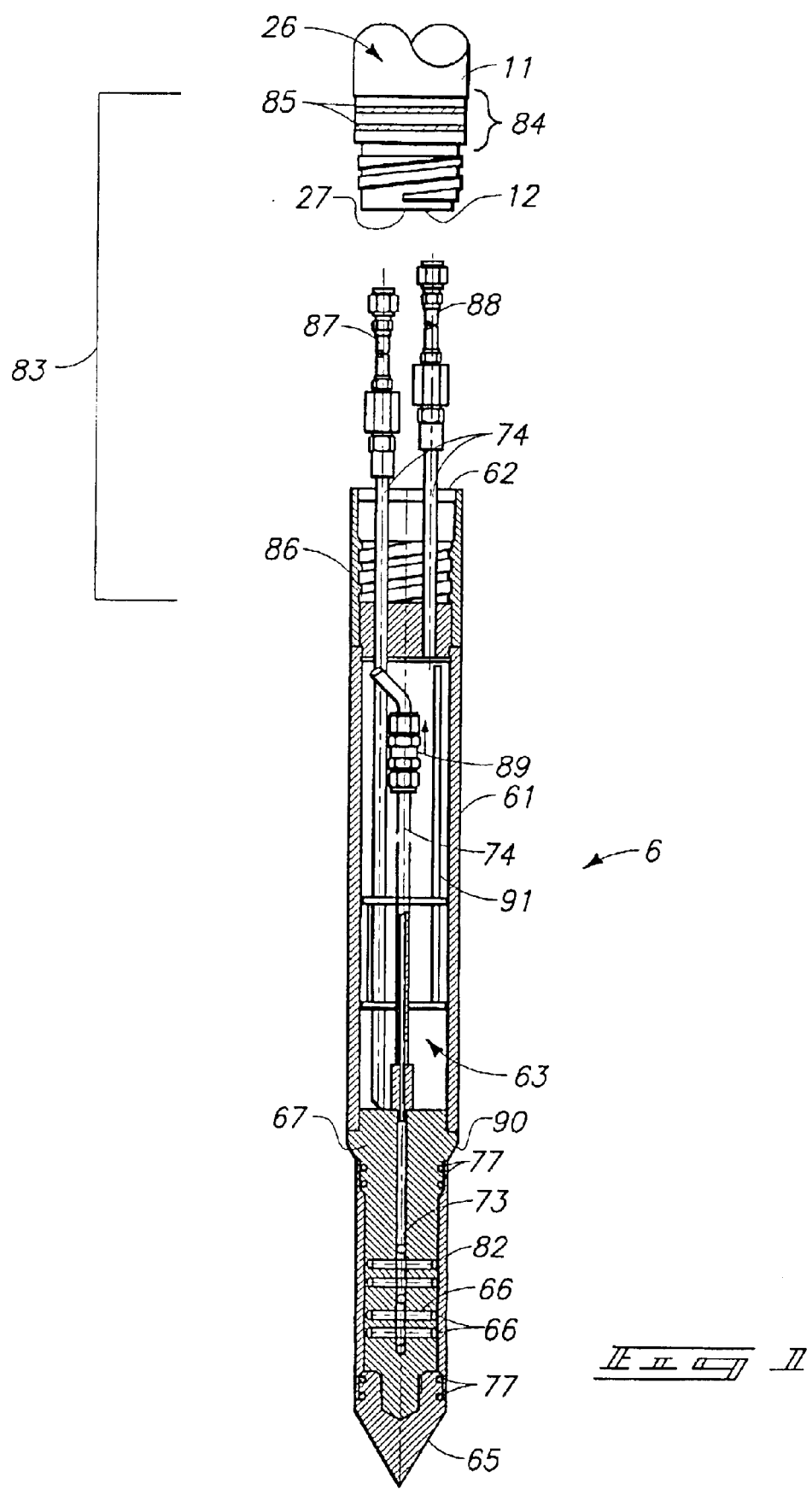
FIG. 1 is a front elevational view, partly in section, showing a lysimeter in accordance with one embodiment of the present invention, and also showing a portion of a probe casing.
Figure 2:
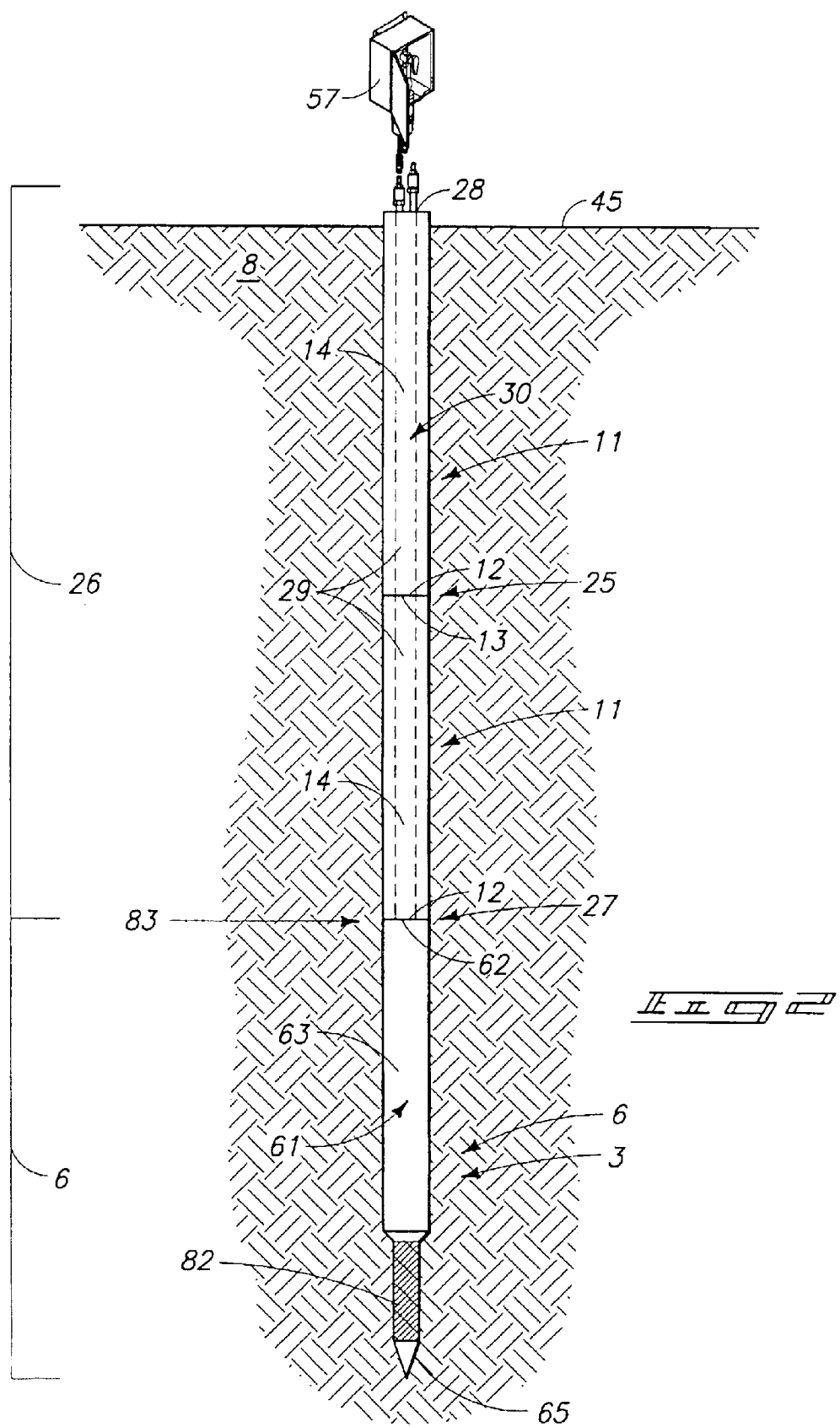
FIG. 2 is a front elevational view, partly in section, showing probe casings and the lysimeter of FIG. 1 positioned for use in a substrate. The lysimeter cap is also shown.

FIGS. 1 and 2 show a lysimeter 6 for sampling subsurface liquids. The lysimeter 6 includes a lysimeter casing 61. The lysimeter casing 61 includes a drive portion 62, a reservoir portion 63, and a tip portion 65. The tip portion 65 includes a sample passageway 66, through which subsurface liquids may be sampled. A fluid conduit 73 is coupled in fluid flowing relation relative to the sample passageway 66, and in operation facilitates the delivery of the sampled subsurface liquids from the sample passageway 66 to the reservoir portion 63 of the lysimeter 6. A plurality of tubes 74 are provided. One of the tubes is a sampling tube that facilitates delivery of the sampled subsurface liquids from the reservoir portion 63 to the land's surface 45 for testing. Another of the tubes 74 is used for applying a vacuum or pressure.

In one embodiment, the sample passageway 66 for sampling subsurface liquids comprises nominal pore openings of about 0.2 micron to about 1 micron through a stainless steel membrane 82; however, other materials and sizes are possible. The stainless steel membrane 82 may be affixed in any appropriate manner. For example, in one embodiment the stainless steel membrane 82 may be welded into place. In the depicted embodiment the stainless steel membrane 82 is held captive by the tip 65. The tip 65 and nose portion 67 shield the stainless steel membrane 82 from large compressive and tensile loads. The nose portion 67 is longer than the membrane 82 and therefore picks up compressive and tensile loading that could otherwise be seen by the membrane 82. O-rings 77 provide a seal. The reservoir portion 63 of the lysimeter 6 has, in one embodiment, a volume of about one liter. However, other volumes are contemplated.

A step 90 provides a compacting function and provides for good contact with the soil. The step is achieved by an increase in diameter or periphery relative to length.

Figure 3:
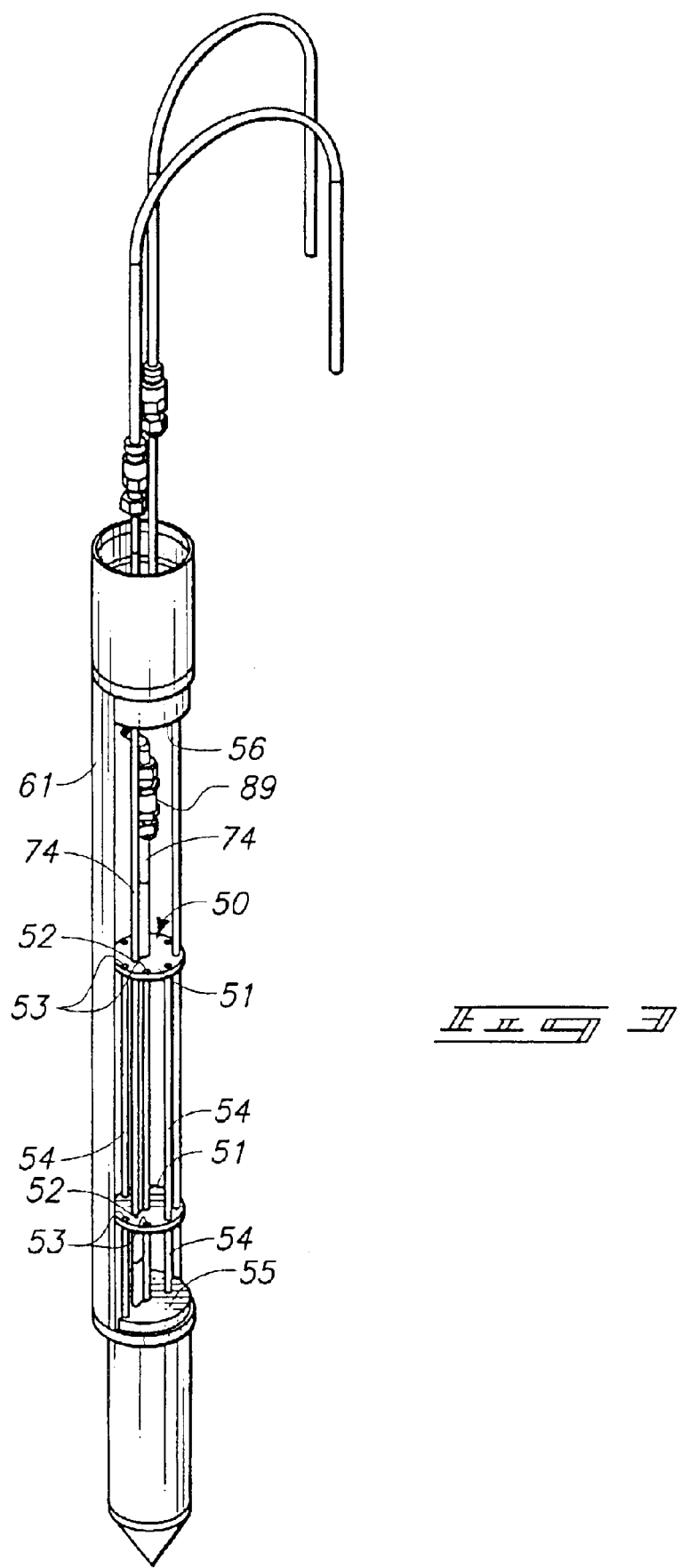
FIG. 3 is a perspective view, partly in section, showing a lysimeter in accordance with one embodiment of the present invention.

FIG. 3 shows construction details of a tube spacer assembly or impact delimiter 50. The spacer 50 absorbs vibration and holds the reservoir sample tubes 74 in place. The spacer 50 is constructed from two thin circular plates or disks 51 that have holes in them. The larger holes 52 are openings for the tubes 74 to pass through. The plates 51 also have smaller holes 53 (which are located proximate the plate's perimeter in the illustrated embodiment) that allow the sample to pass through them. The two plates 51 are connected together by rods 54. In one embodiment, the rods 54 are weld filler rods that are fused to the two disks. In alternative embodiments, the rods are thin rods constructed from wire, thin bar shapes, etc. Using weld filler rod provides for a simple construction. The tube spacer assembly's purpose is to protect the lysimeter components within the upper reservoir 63 from the vibrational loads they would normally experience while the probe is being advanced into the ground. The tube spacer assembly 50 acts as a impact delimiter to absorb vibrational energy and minimize tube 74 lateral deflection. The reservoir tubes 74 will deflect, but the spacer assembly 50 prevents large displacements, which in turn protects tube connection welds, and therefore protects the internal components from shaking themselves apart. The tube spacer assembly 50 is built for flexibility and is a sacrificial component (i.e., is allowed to impact the reservoir's internal cavity walls and deform) so that the internal tube and connection components are not damaged. If the tube spacer assembly 50 is not used, it is possible that the internal reservoir tubing 74 and valve 89 would oscillate within the reservoir 63 during sonic probe advancement, and become bent, damaged, and compromise the lysimeter's function.

The tube spacer assembly 50 utilizes the circular plates (or disks) to absorb energy from lateral vibrational loads. The disks 51 impact the internal reservoir walls and are allowed to plastically deform (i.e., bend), but also prevent the tube components 74 and valve 89 from swinging or experiencing large deflections. The two disks are used along the internal tubing length, to provide uniform displacement control. The extending rods 54 connect the disks 51 together and also are extended within the reservoir to the cavity ends 55 and 56, so that the disks 51 remain in approximately the same position along the reservoir's length. In the illustrated embodiment, the tube spacer assembly 50 is constructed entirely from stainless steel, for maximum corrosion resistance. The weld filler rod is also constructed from stainless steel. In this way, the water sample is not contaminated by the tube spacer within the reservoir 63. The tube spacer assembly 50 could be constructed from other materials as well.

The lysimeter casing 61 shown in FIGS. 1–3 comprises stainless steel. However, any suitable material may be used to construct the lysimeter casing or tubing 61. In one embodiment, the lysimeter casing 61 comprises stainless steel, and is of adequate durability for installation into a substrate by direct push, by sonic drilling, or by a combination of direct push and sonic drilling.

Referring again to FIGS. 1 and 2, the drive portion 62 of the lysimeter casing 61 is configured to selectively couple to the end 12 of a probe casing 11 at a drive connection joint 83 (only a portion of a probe casing 11 is shown in FIG. 1). Stated in other terms, the drive portion 62 of the lysimeter casing 61 is configured to selectively couple to the instrument receiving end 27 of an insertion tube 26 at the drive connection joint 83. The drive connection joint 83 includes a drive connection seal 84 which functions as a substantial barrier to contaminants.

As shown in FIG. 1, in one embodiment, the drive connection seal 84 comprises a plurality of seals. Specifically, in the depicted embodiment, the drive connection seal 84 comprises two seals, such as two o-ring seals 85, which function as a substantial barrier to contaminants. The drive connection joint 83 includes a bearing surface 86 which functions to isolate the drive connection seal 84 and to protect the drive connection seal 84 from large loads as the lysimeter 6 is inserted into the ground 8.

Referring to FIG. 2, a plurality of probe casings 11 are shown coupled in series to form an insertion tube 26 (i.e. two such probe casings 11 are shown). The insertion tube 26 has an instrument receiving end 27 which is configured to selectively couple with the drive portion 62 of the lysimeter casing 61. The insertion tube 26 also has a surface end 28 and an insertion tube wall 29. Together, the instrument receiving end 27, the surface end 28, and the insertion tube wall 29 define a central cavity 30 (shown in phantom lines). A lysimeter cap 57 is configured for ground surface connection and prevents incorrect vacuum pump attachment. The cap 57 is also weather resistant, lending further protection to instruments above ground surface As described above, the plurality of probe casings 11 are selectively coupled to form an insertion tube 26. In the illustrated embodiment, the insertion tube 26 so formed has an outside diameter or periphery of less than four inches. The outer wall or sidewall 14 of the probe casings 11 defines an outside diameter or periphery of the probe casings, which is the same as the outside diameter or periphery of the insertion tube 26 formed when the respective probe casings 11 are selectively coupled (FIG. 2). In one embodiment, the outside diameter of the insertion tube 26 is less than five and five-eighths inches. In one embodiment, the outside diameter of the insertion tube 26 is about two and one-half inches. Other sizes are possible. In one embodiment, the lysimeter casing 61 has an outside diameter or periphery corresponding to the outside diameter or periphery of the probe casings. For example, in one embodiment, the outside diameter of the lysimter casing 61 is less than five and five-eighths inches. In one embodiment, the outside diameter of the lysimeter casing 61 is about two and one-half inches.

As shown in FIG. 1, the instrument receiving end 27 of the insertion tube 26 and the drive portion 62 to the lysimeter casing 61 are configured so that they may be easily coupled. In one embodiment, selectively coupling the instrument receiving end 27 of the insertion tube 26 to the drive portion 62 to the lysimeter casing 61 requires less than four turns to fully engage the drive connection joint 83 and drive connection seal 84. In the depicted embodiment, selectively coupling the instrument receiving end 27 of the insertion tube 26 to the drive portion 62 to the lysimeter casing 61 requires two and one-half turns to fully engage the drive connection joint 83 and drive connection seal 84.

As shown in FIGS. 1 and 2, the insertion tube 26 functions as a conduit through which the plurality of tubes 74 may pass. In operation, one of the tubes 74 can be used to transfer sampled subsurface liquids to the land's surface 45.

The insertion tube 26 and the lysimeter casing 61 are of an adequate durability for installation into the ground 8 by direct push, by sonic drilling, or by a combination of direct push and sonic drilling.

FIGS. 1–3 also depict methods of sampling subsurface liquids. One method includes providing a lysimeter probe 6. The lysimeter probe 6 provided has a lysimeter casing 61 comprising or defined of (in one embodiment) stainless steel. The lysimeter casing 61 includes a drive portion 62, a reservoir portion 63, and a tip portion 65. The tip portion 65 includes a sample passageway 66. An insertion tube 26 is also provided. This insertion tube 26 includes a plurality of probe casings 11 which have been selectively coupled at casing joints 25.

The insertion tube 26 formed by the selectively coupled probe casings 11 has an instrument receiving end 27, a surface end 28, and an insertion tube wall 29 which together define a center cavity 30. The instrument receiving end 27 of the insertion tube 26 and the drive portion 62 of the lysimeter casing 61 are selectively coupled at a drive connection joint 83. The drive connection joint 83 includes a drive connection seal 84 which functions as a substantial barrier to contaminants. A fluid conduit 73 which is coupled in fluid flowing relation relative to the sample passageway 66 is provided. In operation, the fluid conduit 73 facilitates the delivery of sampled subsurface liquids from the sample passageway 66 to the reservoir portion 63. The sampling tubes 74 are coupled in fluid flowing relation relative to the reservoir portion 63, and extend through the center cavity 30 of the insertion tube 26, to facilitate delivery of the sampled subsurface liquids from the reservoir portion 63 to the land's surface 45 for testing. The tubes typically include at least one-vacuum tube 88 and one sample tube 87.

The insertion tube 26 and selectively coupled lysimeter 6 are placed into the ground 8 by direct push, by sonic drilling, or by a combination of direct push and sonic drilling. According to one method, the lysimeter 6 is placed into the ground 8 to a desired depth. One method includes driving the lysimeter 6 into the ground 8 so that the membrane 82 will be in contact with subsurface liquids. Vacuum pressure is then provided to the vacuum tube 88 to pull a sample of the subsurface liquids into the reservoir portion 63 of the lysimeter 6. Air pressure is provided to the air tube 88 to push the sample of subsurface liquids elevationally upwards through the sample tube 87. The air pressure closes a check valve 89 to prevent a sample from being blown out through the sample passageway 66. The check valve 89 is omitted in alternative embodiments, such as in deep installations.

A lysimeter has been disclosed that, in one embodiment, is of all stainless steel construction for corrosion resistance and longevity, with a porous stainless steel membrane design. The tip design isolates and protects the porous membrane from large tension and compression loads during probe installation. The design allows for easy replacement of or size selection for the porous membrane (as required). A robust design has been disclosed for large load (i.e., direct push, sonic, or a combination) emplacement through difficult materials (such as hardened soils, concrete, steel, other metals, etc.) The entire lysimeter is put in place with one action (there are not multiple parts), in one embodiment. A double (redundant) o-ring design impedes contamination transfer. An inner spacer component protects sampling instrumentation from excessive vibrations. The lysimeter is designed for ground retraction, instrument and/or tip replacement, and reuse. A lysimeter cap is configured for ground surface connection and prevents incorrect vacuum pump attachment. The cap is also weather resistant, lending further protection to instruments above ground surface.

The invention provides robust lysimeters that are particularly useful for driving into highly contaminated waste, as well as other uses. The lysimeters can be driven into difficult materials (e.g., hardened soils, concrete, steel, other metals, etc.) that would typically damage other tools. In the illustrated embodiments, small diameter designs are employed that require less energy for installation into a sample. Reduced energy requirements allow for smaller driving equipment resulting in lower cost.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An apparatus for sampling fluid percolating through below-grade strata, from a location at or above grade, comprising:

an insertion tube defined by a tube wall which has an outside diametral dimension and which further has a first instrument receiving end which is positioned below-grade and advanced to a given location in a below-grade strata, and a second, surface end which is positioned at or above grade, and wherein the insertion tube defines a cavity which extends between the first and second ends of the insertion tube;

a lysimeter casing having a first drive portion which is threadably affixed to the first instrument receiving end of the insertion tube, and an opposite distal end, and wherein the lysimeter casing has an inner facing wall which defines a reservoir, and a cavity, and wherein the lysimeter casing has an outside diametral dimension which is not greater than the outside diametral dimension of the insertion tube;

a spacer assembly having first and second spaced disks, and which are individually received in the cavity which is defined by the lysimeter casing, and wherein the respective spaced disks are joined to each other, and further have apertures formed therein;

a plurality of tubes received in the cavity which is defined by the insertion tube, and which extend though the apertures defined by the spacer assembly and into the cavity which is defined by the lysimeter casing, and wherein the respective tubes couple the reservoir in fluid flowing relation to a location which is positioned above grade;

a nose portion immoveably mounted on the distal end of the lysimeter casing, and wherein the nose portion has a proximal end which defines a step having a first diametral dimension, and an opposite, distal end which has a second diametral dimension which is less than the first diametral dimension, and wherein at least one fluid passageway is defined by the nose portion and which couples the nose portion in fluid flowing relation relative to the reservoir, and wherein a region of the nose portion intermediate the proximal and distal ends thereof has an outside diametral dimension which is less than the outside diametral dimension of the insertion tube;

a membrane received about the region of the nose portion which is intermediate the proximal and distal ends of the nose portion, and which permits the passage of fluid therethrough, and wherein the outside diametral dimension of the membrane is less than the outside diametral dimension of the insertion tube; and an earth engaging tip matingly coupled to the distal end of the nose portion, and wherein the maximum outside diametral dimension of the earth engaging tip is substantially equal to the outside diametral dimension of the membrane, and wherein the membrane is captured between the earth engaging tip and the step of the nose portion, and wherein fluid percolating through the below-grade strata passes through the membrane and into the fluid passageway defined by the nose, and wherein the fluid may be withdrawn from the reservoir by the plurality of tubes from the location which is above grade.

2. An apparatus as claimed in claim 1, and wherein the nose portion has a length dimension, and the membrane has a length dimension which is less than the length dimension of the nose portion.

3. An apparatus as claimed in claim 2, and wherein the maximum outside diametral dimension of the earth engaging tip portion, the length dimension of the nose portion, and the step which is defined by the nose portion substantially shields the membrane from compressive and tensive loads.

4. An apparatus as claimed in claim 1, and wherein seals are positioned between the membrane and the earth engaging tip portion, and the nose portion.

5. An apparatus as claimed in claim 1, and wherein a seal is disposed between the first instrument receiving end of the insertion tube, and the drive portion of the lysimeter casing.

6. An apparatus as claimed in claim 1, and wherein the lysimeter casing has an inside diametral dimension, and wherein the first and second spaced disks each have an outside diametral dimension which is less than the inside diametral dimension of the lysimeter casing, and wherein the respective first and second spaced disks impede the lateral deflection of the tubes which couple the reservoir in fluid flowing relation to the location which is positioned above grade.

7. An apparatus for sampling fluid percolating through a below-grade strata, from a location at or above grade, comprising:

an insertion tube defined by a tube wall which has an outside diametral dimension and which further has a first instrument receiving end which is positioned below grade, and an opposite second end which is positioned at or above grade, and wherein the insertion tube defines a cavity which extends between the first, instrument receiving end, and the second end of the insertion tube;

a lysimeter casing having a first end mounted on the instrument receiving end of the insertion tube, and an opposite second end, and wherein the lysimeter casing defines an internal cavity and a reservoir, and wherein the outside diametral dimension of the lysimeter casing is substantially equal to the outside diametral dimension of the insertion tube;

at least one tube which couples the reservoir with the location above grade, and wherein the tube extends through the cavities defined by the respective lysimeter casing and the insertion tube;

a nose portion mounted on the second end of the lysimeter casing, and wherein the nose portion defines a step which is positioned adjacent to the second end of the lysimeter casing, and wherein the step has a maximum outside dimension which is substantially equal to the outside diametral dimension of the insertion tube, and wherein the outside diametral dimension of the step diminishes when measured in a direction which extends substantially longitudinally outwardly relative to the second end of the lysimeter casing, and wherein the nose portion further includes a distal end, and an intermediate portion which is located between the distal end and the step, and wherein the outside diametral dimension of the intermediate portion is less than the maximum outside diametral dimension of the step, and wherein the nose portion defines at least one fluid passageway which extends from the intermediate portion of the nose portion and which is coupled in fluid flowing relation relative to the reservoir;

a membrane disposed in covering relation relative to the intermediate portion of the nose portion, and wherein the membrane has an outside diametral dimension which is less than the maximum outside diametral dimension of the step; and an earth engaging tip mounted on the distal end of the nose, and wherein the maximum outside diametral dimension of the tip is substantially equal to the outside diametral dimension of the membrane, and wherein force applied to the insertion tube from a position above-grade causes the apparatus to form a bore hole in the below-grade strata, and wherein the bore hole is formed, in part, by the earth engaging tip, and wherein the membrane remains substantially in contact with the below-grade strata, and wherein the bore hole is further formed, in part, by the step.

8. An apparatus as claimed in claim 7, and further comprising:

a spacer assembly received in the lysimeter casing, and wherein the at least one tube is received through the spacer assembly, and wherein the spacer assembly impedes lateral deflection of the tube as the apparatus is advanced in the below-grade strata to form the bore hole.

9. An apparatus as claimed in claim 7, and wherein compressive and tensive loads are experienced by the earth engaging tip, and the nose portion as the apparatus is advanced in the below-grade strata to form the bore hole, and wherein the earth engaging tip and the nose portion substantially shields the membrane from the compressive and tensive loads experienced by the earth engaging tip, and the nose portion.

10. An apparatus as claimed in claim 7, and wherein a seal is positioned between the instrument receiving end of the insertion tube and the first end of the lysimeter casing.

11. An apparatus as claimed in claim 7, and wherein a seal is positioned between the membrane and the intermediate portion of the nose portion.

* * * * *